US010088416B2

(12) United States Patent
Niiranen et al.

(10) Patent No.: US 10,088,416 B2
(45) Date of Patent: Oct. 2, 2018

(54) METHOD AND DEVICE FOR DETERMINING GAS COMPONENT INSIDE A TRANSPARENT CONTAINER

(71) Applicant: Oy Sparklike Ab, Helsinki (FI)

(72) Inventors: Kai Niiranen, Järvenpää (FI); Miikkael Niemi, Espoo (FI); Mikko Syrjälahti, Espoo (FI)

(73) Assignee: Oy Sparklike Ab, Helsinki (FI)

( * ) Notice: Subject to any disclaimer, the term of this patent is extended or adjusted under 35 U.S.C. 154(b) by 20 days.

(21) Appl. No.: 15/111,824

(22) PCT Filed: Jan. 14, 2015

(86) PCT No.: PCT/FI2015/050016
§ 371 (c)(1),
(2) Date: Jul. 15, 2016

(87) PCT Pub. No.: WO2015/107264
PCT Pub. Date: Jul. 23, 2015

(65) Prior Publication Data
US 2016/0334331 A1    Nov. 17, 2016

(30) Foreign Application Priority Data

Jan. 15, 2014   (FI) ..................................... 20145030

(51) Int. Cl.
*G01N 21/39*   (2006.01)
*G01J 3/433*   (2006.01)
*G01N 21/27*   (2006.01)

(52) U.S. Cl.
CPC .............. *G01N 21/39* (2013.01); *G01J 3/433* (2013.01); *G01N 21/274* (2013.01); *G01J 3/4338* (2013.01); *G01N 2021/399* (2013.01)

(58) Field of Classification Search
CPC .................................. G01N 21/39; G01J 3/433
(Continued)

(56) References Cited

U.S. PATENT DOCUMENTS 3,790,797 A   2/1974 Sternberg et al.
4,730,112 A   3/1988 Wong
(Continued)

FOREIGN PATENT DOCUMENTS

CN   101315328 A   12/2008
EP   0417884 A2    3/1991
(Continued)

OTHER PUBLICATIONS

Smith et al., Sep. 23, 2013, vol. 21, No. 19.
(Continued)

*Primary Examiner* — Roy M Punnoose
(74) *Attorney, Agent, or Firm* — Berggren LLP

(57) ABSTRACT

A device for non-invasively determining existence of a gas component of interest inside a determination space of a glass unit comprises a laser beam emitting unit comprising a laser source for emitting laser beam towards said measuring space and detecting unit comprising a detector for detecting transmission of said emitted laser beams traveled through said space. The device is configured to measure in a calibration mode locations of at least one reference peak of at least same gas component as to the determined inside the determination space. The emitted laser beam is configured to travel through a calibration space having at least the gas component of interest, and the detecting means is configured essentially to detect or image said beam transmitted through said calibration space. The device is also configured to be moved so to receive said determination space between the laser beam emitting unit and detecting unit for a determining purpose of the existence of the interest gas component inside said determination space.

19 Claims, 3 Drawing Sheets

(58) Field of Classification Search
USPC .......................................................... 356/437
See application file for complete search history.

(56) References Cited

U.S. PATENT DOCUMENTS

| | | | |
|---|---|---|---|
| 5,317,156 A * | 5/1994 | Cooper | G01N 21/39 |
| | | | 250/339.13 |
| 5,331,409 A | 7/1994 | Thurtell et al. | |
| 5,334,536 A | 8/1994 | Nonnenmacher | |
| 5,821,537 A | 10/1998 | Ishihara et al. | |
| 6,639,678 B1 | 10/2003 | Veale | |
| 7,414,726 B1 | 8/2008 | Bambeck | |
| 7,705,988 B2 * | 4/2010 | Richman | G01J 3/4338 |
| | | | 356/432 |
| 8,149,407 B1 | 4/2012 | Rao | |
| 9,316,627 B2 * | 4/2016 | Niiranen | G01N 33/0006 |
| 2006/0044562 A1 | 3/2006 | Hagene | |
| 2007/0131882 A1 * | 6/2007 | Richman | G01J 3/4338 |
| | | | 250/573 |
| 2008/0198027 A1 * | 8/2008 | Bugge | G01N 21/3504 |
| | | | 340/632 |

FOREIGN PATENT DOCUMENTS

| | | |
|---|---|---|
| EP | 2000792 A1 | 12/2008 |
| EP | 2372344 A1 | 10/2011 |
| GB | 2412728 A | 10/2005 |
| JP | S58225345 A | 12/1983 |
| JP | H0792081 A | 4/1995 |
| WO | 2005111585 A2 | 11/2005 |
| WO | 2008053507 A2 | 5/2008 |
| WO | 2011007047 A1 | 1/2011 |
| WO | 2012156589 A1 | 11/2012 |

OTHER PUBLICATIONS

Finnish patent application No. 20145030, Office Action dated Oct. 4, 2017.
Cocola L: "Tunable diode laser absorbtion . . . " University of Padova, publ. Jan. 27, 2012.
Supplementary European Search report issued on EP application No. 15737595.7 dated Aug. 23, 2017.
Finnish Patent and Registration Offce, Search Report dated Sep. 19, 2014 related to FI20145030.

* cited by examiner

METHOD AND DEVICE FOR DETERMINING GAS COMPONENT INSIDE A TRANSPARENT CONTAINER

TECHNICAL FIELD OF THE INVENTION

The invention relates to a method and device for determining an interest gas component in particularly inside a glass unit of one or several separate cavities, such as insulating glass units, IGUs, or any other similar transparent container.

BACKGROUND OF THE INVENTION

In the glass manufacturing process glass sheets (known as float glass) can be combined with different kind of elements, such as coated or tempered layers to create glass panes for different purposes having specific properties. For example, insulating glass units, IGUs, are constructed typically with a configuration having two or more glass sheets with a closed space in between the sheets, where the closed space is filled with gas with low thermal conductivity, such as Argon, Xenon, Krypton Nitrogen or mixture of those. There is need in the industry to check the quality of the glass unit and ensure that there is no leakage, so that the filling gas has not leaked away.

Different kinds of solutions are known from the prior art for determining the quality and possible leakages of a gas mixture contained in the spacing. For example WO 2012/156589 relates to a non-invasive method for determining a concentration of a gas component in a gas mixture contained in a spacing of a glass unit having at least two glass sheets spaced apart from each other and forming said spacing. In addition SMITH C J ET AL: "Real-time calibration of laser absorption spectrometer using spectral correlation performed with an in-line gas cell", OPTICS EXPRESS, voi. 21, no. 19 (2013 Sep. 17), XP055353294, 001: 10.1364/0E.21.022488 discloses a real-time drift correction and calibration method using spectral correlation based on a revolving in-line gas cell for laser-based spectroscopic trace-gas measurements, and is focused for measuring and especially ensuring accuracy of the concentration measurement over long time.

EP0417884 discloses calibrating a non-dispersive infrared gas analyzer especially adapted for measuring the concentrations of HC, CO and $CO_2$ in a vehicle exhaust is described.

EP2372344 discloses a method for analysing a gaseous component present in a hermetically sealed container, the latter is placed in a measuring station between a laser beam emitter and a receiver. The laser beam is emitted towards the receiver and through the portion of the container, where the gaseous component is located, and the concentration of the gaseous component is inferred by analysing the spectrum of the laser beam absorbed by the gaseous component.

WO2011/007047 discloses a solution where one or more light beams from a light source with defined polarization are directed at a suitable angle to the material surfaces, such as glass panes conveyed on a production line. Reflected beams from the material interfaces are directed through a linear or circular polarizer with defined polarization properties and their positions and intensities are measured while the measurement location is altered. Of the related parameters, the thicknesses of constituent materials are calculated from the reflection positions, interface type from the average reflection intensity and the possible tempering from the intensity fluctuations of the reflections. Also concentration of at least one gas component in a gas mixture contained in a closed spacing between the two layers of said transparent object (for example an insulated glass unit comprising a gas mixture in a closed spacing between the panes in order to minimize heat conduction through the glass unit) can be detected.

U.S. Pat. No. 6,639,678 discloses a system for non-destructive monitoring of gases in sealed containers. The system includes a tunable diode laser (TDLAS) source that provides a uncollimated laser beam for absorption in a substance to be measured. TDLAS determines the concentration of a gas by measuring the amount of light absorbed at a particular wavelength. The intensity of light absorbed is directly related to gas concentration through Beer's law.

US2007/131882 discloses a method of detecting a target gas in a monitored space comprising applying an electrical control current to a laser diode so as to generate optical radiation of a wavelength defined by the control current, transmitting the optical radiation across the monitored space and determining the optical absorption thereof, wherein the control current defines two mean wavelengths $\wedge_1$ and $\wedge_2$ for the optical radiation and includes electrical modulation at two frequencies f and f' respectively, wherein $\wedge_1$ and $\wedge_2$ are respectively close to two separate optical absorption lines of the target gas, and f and f' are not harmonically related.

Coeola L: "Tunable diode laser absorption spectroscopy for oxygen detection", PH.D. THESIS IN SCIENZE TECNOLOGIE E MISURE SPAZIALI (2012 Jan. 27), XP055198219, UNIVERSITY OF PADOVA discloses how the traditionallimits of Tunable Diode Laser Absorption Spectroscopy are addressed with digital signal processing techniques and careful optical design towards the realization of gas sensing instruments with the stability, robustness and reliability that are required in an industrial environment.

Typically these solutions are based on measuring concentration of the gas components in the gas mixture contained in the spacing, such as measuring absorption peak of the filling gases and thereby the concentration of the filling gas. However, the concentration measurements of the filling gas has some drawbacks, namely for different types of filling gas a different laser source must be used, which is clearly expensive and time consuming way to measure. Another drawback is that the gas volume inside the typical glass unit is very small, whereupon the amount of the gas to be measured is small and thereby also the absorption peak (amplitude of the peak) caused by said gas component to the measuring beam is very weak. In addition, and therefore, the location of the absorption peak of the gas component to be measured might be very hard to find from the measured signal due to environmental noise, which easily covers the absorption peak to be determined and thus makes the analysis very cumbersome and labour.

SUMMARY OF THE INVENTION

An object of the invention is to alleviate and eliminate the problems relating to the known prior art. Especially the object of the invention is to provide a method for performing a non-invasive determining of a quality of a glass unit or leakage of a gas component contained in a spacing of a glass unit or other transparent container or space.

The object of the invention can be achieved by the features of independent claims.

The invention relates to a device for non-invasively determining an existence gas component of interest inside a space and thereby any leakage of the space.

According to an embodiment a device for non-invasively determining existence of a gas component of interest inside a determination space of a glass unit comprises a laser beam emitting unit and detecting unit. The laser beam emitting unit comprises advantageously a laser source for emitting laser beam towards said determination space. The detecting unit comprises a detector for detecting transmission of the emitted laser beams traveled through said determination space. In addition the device comprises also a calibration mode.

The device is configured to measure in the calibration mode at least a same gas component and advantageously locations of at least one reference peak of the same gas component as to be determined inside the determination space. In the calibration mode the emitted laser beam is configured to travel through a calibration space having at least the gas component of interest. The detecting means is configured to detect or image the beam transmitted through the calibration space. It is to be noted that even if the device and the method comprises the calibration mode, there is no need for performing said calibration before every single determination measurement of the existence gas component of interest. Advantageously the calibration mode is performed only when necessary, which may be for example when the device is set on or once in a day or the like, but of course it is also possible to perform the calibration mode with every determination and measurement.

In addition for determination purpose the device is moved so to receive the determination space between the laser beam emitting unit and detecting unit for a determining the existence of the interest gas component inside the determination space.

The determined space where the gas component is to be determined is typically a space of the insulating glass units, IGUs, where the space is closed by the glass sheets of the unit. Anyway the determination space might also be any other determination space or transparent container.

The calibration space used for the calibration may comprise a calibration chamber having the same gas component of interest, such as $O_2$ for example. According to an embodiment the calibration chamber is advantageously arranged between the emitting and detecting units so that the emitted beams travels through said calibration chamber before received by the detector. According to an embodiment the device may comprise said calibration chamber inside one of the units, whereupon the calibration chamber is configured to be moved so that the emitted beams travels through said calibration chamber before received by the detector. Still according to an embodiment the calibration space may be free air between the emitting and detecting units, especially if the gas component of interest is a gas component comprised by the free air, such as $O_2$.

It is to be noted that the gas component used in the calibration mode may be e.g. same as the filling gas of the determination space, if the filling gas is measured. However, it is to be noted than in many case another gas than the filling gas is much easier to determine for leakages. Especially it is to be noted that if the glass unit has any leakage, the filling gas will leak away, but at the same time gas components of the surrounding air will diffuse or flow into the space of the glass unit. Thus the gas component to be measured and contained also in the calibration chamber or free air might be e.g. $O_2$ or $CO_2$, as an example, and not necessarily the gas component of filling gas, such as Argon, Xenon, Krypton Nitrogen or mixture of those. If the measuring reveals the existing for example of Oxygen inside the glass unit, the leakage may be determined. According to an embodiment the calibration chamber may be filled with normal air having e.g. 21% of $O_2$ or free air between the units can be used. Again it is to be noted that a number of different chambers with different gas component can be used.

According to an advantageous embodiment the detecting means is configured to determine or image said transmitted beam for analysing. The detecting means advantageously provides electrical signal corresponding an intensity of the measured beam.

In the calibration process an electric feed current of the laser source is changed (WMS technique) in order to scan the peak location of the gas component to be determined. When starting the calibration process, the current is increased so to change the wavelength of the emitted laser beam. At the same time the current may be modulated by a sinusoidal signal in order to strengthen and make more reliable the signal to be determined. The current is increased to a certain limit so that the peak location caused by the absorption of the gas component to be measured is determined. Then the current is again decreased so the overlap the emitted wavelength of the laser source around the peak to be determined. Thus the peak location can be detected in the function of wavelength and/or the electric feed current of the laser source. As a result a peak pair is achieved.

It is to be noted that the measurement or determination of the existence of the interest gas component can be done even if only the location of the peak is known and there is no need for calibrating the device so that to derive absolute concentration of the gas of interest. Thus the calibration should be understood as to seeking the locations of reference peak(s) of the gas component of interest. Typically the determination of the location of the peak is enough, especially if it is determined whether there is any leakage and if any environment gas has got inside the space. If there is leakage, only small signal at the location of said peak reveals the leakage and thus there is no need to know the absolute concentration of the measured gas component. Anyway it is to be also noted that if needed, the calibration may also be carry out so that the absolute concentrations can be measured. For this the different transparent containers with different concentration of the gas component inside these containers are measured in order to achieve different responses for different concentrations. Again the absolute concentration of the gas component inside the calibration chamber is not important, but it is used only the determining the location of the peak(s) of the gas to be measured.

According to an embodiment the laser beam emitting unit and detecting unit are encapsulated by hermetically sealed housing separately. The housings are advantageously filled with shielding gas, such as nitrogen or argon, for example, which is selected to be inert for the laser wavelength used. The housing is additionally emptied essentially from the gas to be measured so that it would not interfere the measurement.

According to an embodiment the device is configured to perform a self-check advantageously before measurements. In the self-check the device is configured to measure a volume inside the device housings. In the self-check the emitting and detecting units are interfaced to each other so that no determination space or calibration space are involved. Thus, if there is any leakage in the housings, it would be noticed.

According to an embodiment the device is configured to change a temperature of the laser emitting means so to adjust the distance of the peak in the measured curve when scanning the wavelengths around the peak location of the gas component to be measured. By this the distance of the peaks can be changed in an advantageous position so that the peaks are not covering each other and that the best resolution is achieved. As an example the device may comprises a heating means, advantageously controllable heating means, such as a peltier element. The heating means is advantageously configured to manage temperature of the device and especially temperature of the laser emitting means, such as tunable diode laser.

In addition, according to an embodiment the device may also comprise an interfacing means, such as a sealing member, such as silicone sealing for example, which is configured to be introduced on the surface of the determination space of interest. In addition the device may comprise an underpressure providing means configured to provide underpressure in the volume between said device and the surface of the determination space defined by said interfacing means so to remove air between the device and the space, and to secure said device to said surface and thereby facilitating the positioning of the device e.g. essentially perpendicular to said surface and thereby minimizing measuring errors due to misaligned positioning. The device may also comprise a shielding gas providing means configured to provide shielding gas in the volume between said device and the surface of the space defined by said interfacing means and thereby remove any interfering gas components. Due to removing the air any possible interfering gas components are removed whereupon more accurate measuring results can be achieved.

Furthermore, according to an embodiment, the device may also be configured to determine the thickness or locations of different layers of the determination space and/or the path length of the laser beam inside said determination space path length of the laser beam. This is advantageously implemented by measuring also reflections from the interfaces related to the space to be measured and reflection positions of the reflected beams either on different location on the reflection detecting means, such as on a row detector, or the reflection positions can be determined by the movable detector. The reflection positions reveals location of the layer or interface, where the beam has been reflected and based on known optical trigonometry the thicknesses can be determined.

The gas component in the determination space absorbs a very narrow-line width characteristic for each gas component, and the magnitude of the intensity variation due to absorption is proportional to the concentration of the gas. The intensity variations around or over the absorption line of the interest gas component is very non-linear. In the invention these non-linear variations in the intensity of the reflected or transmitted light beams around or over an absorption line of the interest gas component is then determined for determining the concentration of the gas component.

The absorption signal to be detected in measurements and calibration is advantageously manipulated by WMS or FMS technique, such as by scanning a sinusoidally frequency-modulated diode laser over the absorption feature of the gas component to be determined in order to strengthen the second order polynomial fitted to the non-linear curve representing the variation in the intensity of the detected beams and concentration of the gas component to be detected and/or to minimize the low-frequency noise induced.

The performance of direct absorption is often degraded by the occurrence of 1/f noise. A common way to avoid such low frequency noise of system components, for example 1/f laser excess noise, is to shift the absorption signal to a higher frequency. In TDLAS technique, this can be achieved by a modulation of the diode laser operation current. Such modulation results in a modulation of the instantaneous laser frequency. Upon interaction with the non-linear reflected intensity profile of an absorption line, this will result in a periodic modulation of the detected intensity. This allows detection of absorption signal at the fundamental modulation frequency or its overtones.

For example a sinusoidal modulation of the diode laser operation current results in a sinusoidal wavelength (and amplitude) modulation of the laser output. Interaction with a wavelength-dependent and non-linear reflection signal (e.g. absorption lineshape) results in a periodic, but non-sinusoidal, reflection signal that consists of the modulation frequency itself as well as its harmonic overtones. This can be used in an embodiment to shift the detection frequency to the high frequency region less affected by low frequency noise (e.g. 1/f noise), and thus improving the sensitivity. This is typically achieved by letting a lock-in amplifier measure the amplitude of the harmonic components (most commonly, the second) as the laser is tuned over an absorption line of interest.

The invention offers many advantageous features over the known prior art methods, such as easy internal or external calibration process even before every measurements. In addition according to the invention it is possible to compensate inaccuracies due to temperature adjustment of the laser source affecting to the wavelength of the laser emitted beam and this to measuring data. In addition the invention enables the determinations and measurements even without any accurate knowledge of the concentration of the gas component used in calibration, because essentially only the location(s) of the peak to be measured matters. Furthermore the device of the invention is very reliable, because of the self-check. The calibration process as well as the self-check may be performed automatically and fast even before every measurement.

BRIEF DESCRIPTION OF THE DRAWINGS

Next the invention will be described in greater detail with reference to exemplary embodiments in accordance with the accompanying drawings, in which.

DETAILED DESCRIPTION

Figures 1A, 1B:
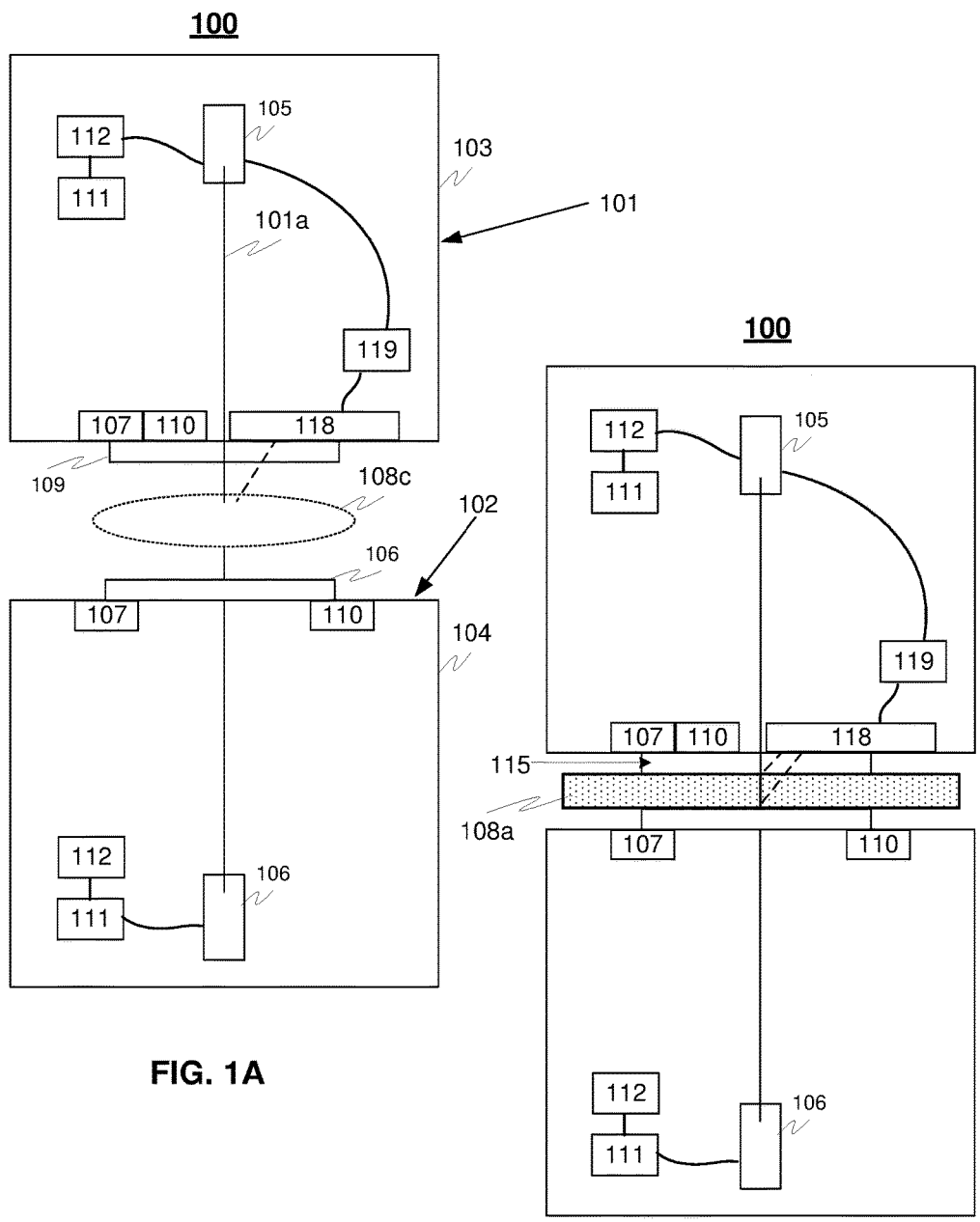
FIGS. 1A-1D illustrates principles of exemplary device in calibration and determination modes according to an advantageous embodiment of the invention.

FIGS. 1A-1D illustrates principles of exemplary device 100 according to an advantageous embodiment of the invention, wherein the device comprises an emitting unit 101 and detection unit 102. The laser beam emitting unit comprises advantageously a laser source 105 for emitting laser beam towards the detecting unit 102, as well as also towards said determination space 113 when performing the determination. The detecting unit 102 comprises a detector 106 for detecting transmission of the emitted laser beams traveled through said determination space, for example. In addition the device comprises also a calibration mode, whereupon the laser beam emitted is configured to be traveled through a calibration space.

It is to be noted that the device or units 101, 102 advantageously comprises also suitable optical means (not shown) emitting and collimating the emitted beam 101a to the determination or calibration space, as well as to collect the beams from the determination or calibration space to said detector 106.

Figures 1C, 1D:
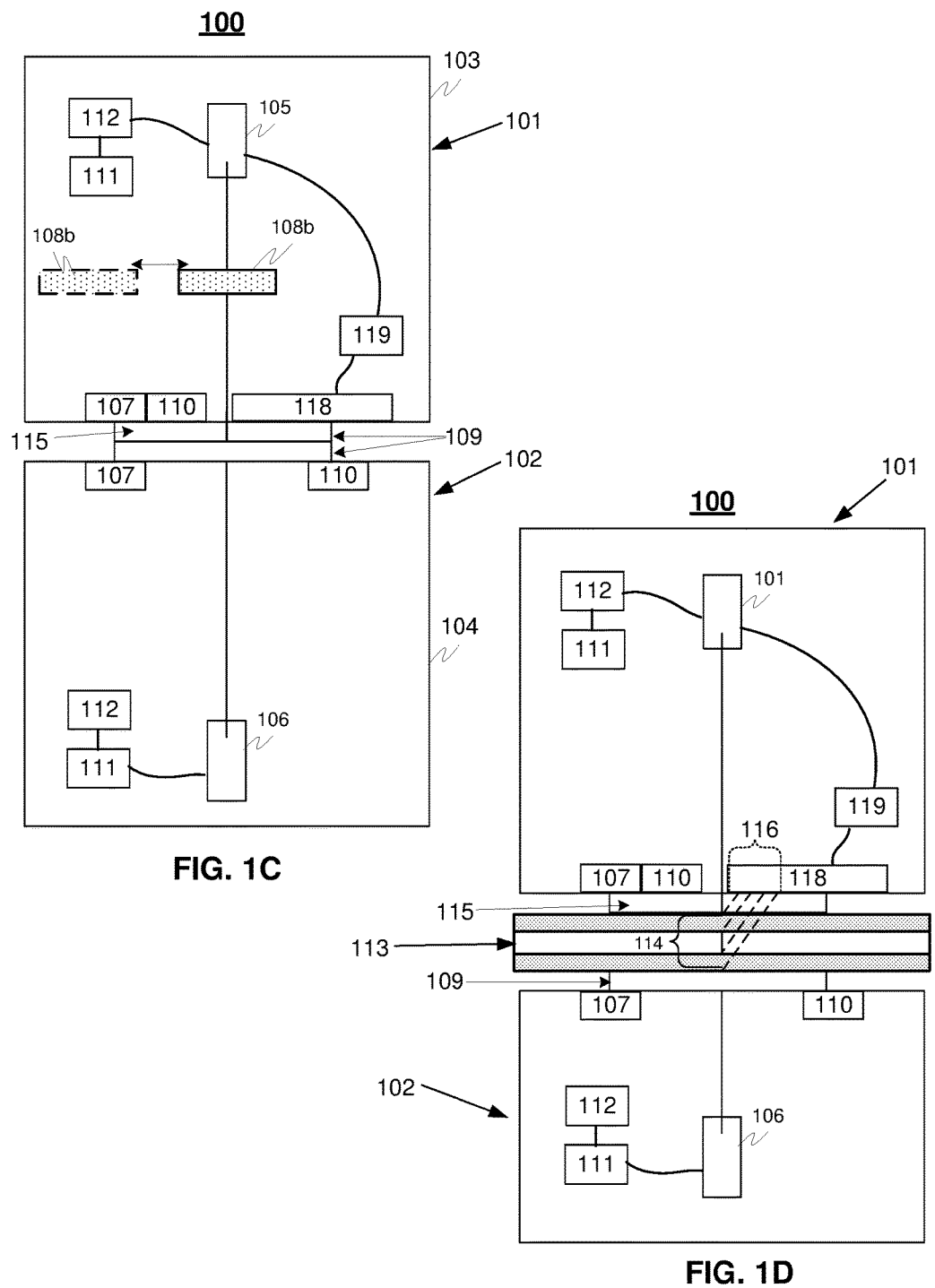

The calibration space used for the calibration may comprise a calibration chamber having the same gas component of interest. FIG. 1B describes the arrangement, where the calibration chamber 108a is arranged between the emitting and detecting units 101, 102 so that the emitted beams 101a travels through said calibration chamber 108a before received by the detector 106. FIG. 1C describes the arrangement, where the calibration chamber 108b is arranged inside the emitting unit 101, so that for calibration the calibration chamber 108b is configured to be moved so that the emitted beam 101a travels through said calibration chamber 108b before received by the detector 106. It is to be noted that the calibration chamber 108b may also be located in the detecting unit 102, respectively. In this embodiment the units 101, 102 are advantageously interfaced against each other so that they are not detecting any outer signals. In addition, FIG. 1A describes the arrangement, where the calibration space used is a space 108c of free air between the units 101, 102.

For a determination purpose the device 100 is moved so to receive the determination space 113 between the laser beam emitting unit 101 and detecting unit 102 for a determining the existence of the interest gas component inside the determination space 113, as is illustrated in FIG. 1D.

Also a self-check may be done, where a volume inside the device housing 103, 104 is measured, as is illustrated in FIG. 1C, when the calibration chamber 108b is moved away so that it is not involved in the measurement. If no signal is detected from said volume, there are no leakages and the housing and the shielding gas inside the housing is working properly. Advantageously the housing is a hermetically sealed housing encapsulating the emitting and detecting units 101, 102.

The device may also comprise an interfacing means 109, such as a sealing member, such as silicone sealing for example, which is configured to be introduced on the surface of the determination space 113 of interest, or on the surface of the calibration chamber 108a, if it is used. In addition the device may comprise an underpressure providing means 107, such as a vacuum pump, configured to provide underpressure in the volume 115 between said device 100 and the surface of the determination or calibration spaces so to remove interfering air from the volume, as well as to secure the device to said surface and thereby facilitating the positioning of the device e.g. essentially perpendicular to said surface and thereby minimizing measuring errors due to misaligned positioning. The device may also comprise a shielding gas providing means 110 configured to provide shielding gas in the volume 115 and thereby remove any interfering gas components.

Figure 2:
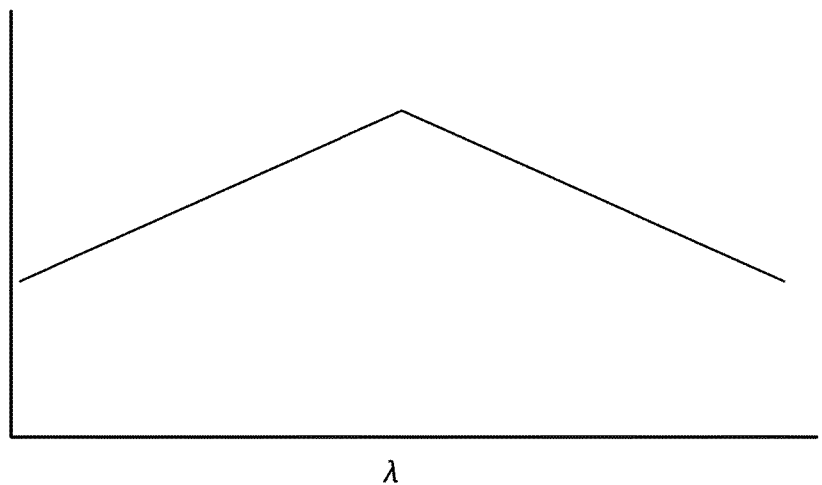
FIG. 2 illustrates exemplary principles of a calibration and measuring methods according to an advantageous embodiment of the invention.
Figure 3:
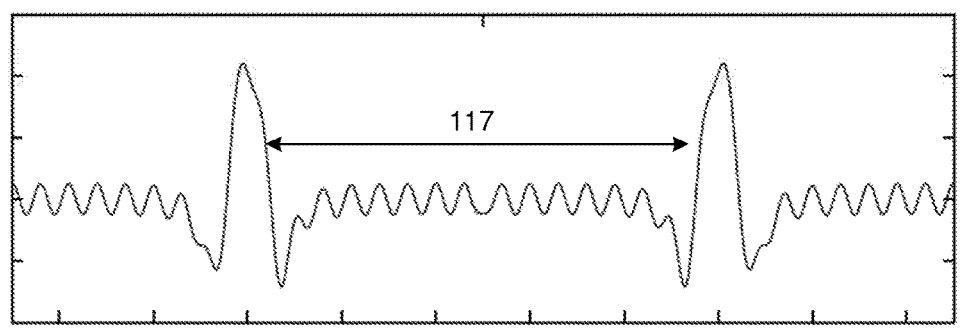
FIG. 3 illustrates exemplary measured curve according to an advantageous embodiment of the invention.

In addition the device may comprise controlling means 112 for controlling the operation of the device, such as movements of the calibration chamber 108b, and the operation of the laser beam emitting means 105. As an example the controlling means 112 may control the electric current of the laser source 105 so to scan the wavelength area around the gas of interest. In the calibration process as well as also in determination process the current is changed, as can be seen in the curvature of FIG. 2, where the wavelength of the emitted beams are changed in the function of feed electric current of the laser source. FIG. 3 illustrates a measured curve, where the peak induced by the gas of interest can be found essentially at the same wavelength. These locations of peak (wavelength, or in practice the electric current of the laser source enabling said wavelength) is then used in determination of the gas of interest in said space 113.

Furthermore the device may also comprise temperature managing means 111, such as a peltier element, which is configured to change a temperature of the laser emitting means 105. By changing the temperature the distance 117 of the peaks in the measured curve can be adjusted when scanning the wavelengths around the peak location.

The distance (displacement) 114 of the reflection points where the portion of the emitted beam is reflected can be easily determined for thickness measurement. For thickness measurement the reflections from the interfaces related to the space to be measured and reflection positions 116 of the reflected beams either on different location on the reflection detecting means, such as on a row detector 118 can be determined. As can be seen in FIG. 1D, the reflection positions reveal location of the layer or interface where the beam has been reflected and based on known optical trigonometry the thicknesses or other distances can be determined.

The device advantageously comprise also a data processing unit 119, which is configured to perform any calculations and determinations of the measured intensities, as well as the thickness, distances and also path length of the beams and order of interfaces or surfaces caused the reflections of the beam. In addition the data processing unit 119 may be configured to determine possible existence of the gas of interest inside the measured space and thereby also any possible leakages, and correspondingly to perform any indication of leakage, such as an alarm.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. Even though only a glass unit is described above, it is to be noted that different kinds of reflective transparent objects can be determined, such as for example a glass or plastic, such as float glass, laminated glass, toughened or tempered glass, especially an insulating glass or glass coated with a coating, for instance an electrically conductive coating, as well as also other transparent containers. It is to be noted that the laser beam is advantageously emitted in a certain angle towards the space and interfaces or surfaces so that to minimize possible interferences disturbing the measurements, even if this is not clearly shown in the Figures due to clarity.

The invention claimed is:

1. A device for non-invasively determining existence of a gas component of interest inside a determination space being separate from the device, wherein the device comprises:
   a laser beam emitting unit comprising a wavelength tunable laser source for emitting laser beam towards said determination space, a detecting unit comprising a detector for detecting transmission of said emitted laser beam traveled through said determination space, wherein
   the device comprises a calibration space and wherein the device is configured to measure locations of at least one reference peak of at least a same gas component as to be determined inside the determination space without determining a concentration, wherein said emitted laser beam is configured to travel through the calibration space having at least the gas component of interest, and wherein the detecting unit is configured to detect or image said beam transmitted through said calibration space, and said device is configured to receive said determination space between the laser beam emitting unit and the detecting unit for determining only existence of the gas component of interest inside said determination space by comparing whether the measurement of the determination space induces a peak at the same location as said reference peak or not, without determining the concentration of the interest gas component.

2. The device of claim 1, wherein the laser beam emitting unit and the detecting unit comprise hermetically sealed housings encapsulating both of said units separately, said housing being filled with shielding gas being inert for the laser wavelength and emptied essentially from the gas of interest.

3. The device of claim 2, wherein said device is configured to perform a self-check, where said detecting unit is configured to measure a volume inside said device housings so said units are configured to be interfaced to each other and so that no determination space or calibration space are involved.

4. The device of claim 1, wherein said calibration space comprises a) free air or b) a calibration chamber comprising said gas component of interest, and arranged between said units, or c) wherein the device comprises a calibration chamber inside one of the units, and said calibration chamber is configured to be moved so that the emitted beams travel through said calibration chamber before received by the detector.

5. The device of claim 1, wherein the device is configured to change an electric current of the laser source in order to scan wavelengths around an assumed peak of the gas component to be determined in calibration process in order to determine accurate location of said peak in the function of electric feed current of the laser source, whereupon the device is configured to use said wavelengths or peak locations also in measuring process for determining the gas component inside the determination space.

6. The device of claim 1, wherein the device is configured to change a temperature of the laser source so to adjust distance of peaks in a measured curve when scanning the wavelengths around the peak location of the gas component to be measured.

7. The device of claim 1, wherein the device comprises interfacing means configured to be limited on a surface of the determination space to be received for measuring, said interfacing means thereby defining a volume between the device and the surface of the determination space to be received, and an underpressure providing means configured to provide underpressure in the volume between said device and the surface of the determination space defined by said interfacing means.

8. The device of claim 1, wherein the device comprises interfacing means configured to be introduced on the surface of the determination space to be received for measuring, said interfacing means thereby defining a volume between the device and the surface of the determination space to be received, and a shielding gas providing means configured to provide shielding gas in the volume between said device and the surface of the determination space defined by said interfacing means.

9. The device of claim 1, wherein the device comprises also a reflection measurement detector, which is configured to determine location of reflections of the emitted beam from interfaces of the determination space locating at different depths in the determination space and thereby configured to determine thickness of the different layers of the determination space or the path length of the laser beam inside said determination space.

10. The device of claim 1, wherein the device comprises a heating means, which is configured to manage temperature of the device and temperature of the laser emitting means.

11. The device of claim 4, wherein said calibration space comprises $O_2$ gas.

12. The device of claim 10, wherein the heating means is a peltier element.

13. The device of claim 10, wherein the laser emitting means is a tunable diode laser.

14. A method for non-invasively determining existence of a gas component of interest inside a transparent determination space being separate from the device, wherein a laser beam is wavelength modulated and emitted towards said determination space by an emitting unit comprising a wavelength tunable laser source and transmission of said emitted laser beams traveled through said determination space is detected by a detecting unit comprising a detector, wherein a calibration is performed in relation to said determination, wherein locations of at least one reference peak of at least a same gas component as to be determined inside the determination space without determining a concentration is measured so that said emitted laser beam travels through a calibration space having at least the gas component of interest, and wherein the detecting unit is configured to detect or image said beam transmitted through said calibration space, and said determination space is received between the laser beam emitting unit and detecting unit for a determining only existence of the interest gas component inside said determination space by comparing whether the measurement of the determination space induces a peak at the same location as said reference peak or not, without determining the concentration of the interest gas component.

15. The method of claim 14, wherein a self-check is performed, where a volume inside housings of the emitting unit and detecting unit is measured so said emitting unit and detecting units are configured to be interfaced to each other and so that no determination space or calibration space are involved.

16. The method of claim 14, wherein said calibration space comprises a) free air or b) a calibration chamber comprising said gas component of interest, and arranged between said emitting unit and detecting units, or c) wherein a calibration chamber inside one of the emitting unit and detecting units is provided and moved so that the emitted beams travel through said calibration chamber before received by the detector.

17. The method of claim 14, wherein an electric current of the laser source is changed in order to scan the wavelengths around an assumed peak of the gas component to be determined in calibration process in order to determine accurate location of said peak in the function of electric feed current of the laser emitting means, and whereupon said wavelengths or peak locations are used also in determining process for determining the gas component inside the determination space.

18. The method of claim 14, wherein a temperature of the laser emitting means is manipulated so to adjust distance of the peaks in a measured curve when scanning the wavelengths around the peak location of the gas component to be measured.

19. The method of claim 14, wherein an interfacing means of the emitting unit and detecting units is introduced on a surface of the determination space to be received for measuring, said interfacing means thereby defining a volume between the device and the surface of the determination space to be received, and an underpressure is provided into the volume between said emitting unit and detecting units and the surface of the determination space defined by said interfacing means or wherein shielding gas is provided into the volume between said device and the surface of the determination space defined by said interfacing means.

* * * * *